United States Patent
Moore et al.

(10) Patent No.: US 10,143,418 B2
(45) Date of Patent: Dec. 4, 2018

(54) COMBINATION AIRFLOW, SOUND AND PULSE WAVE SENSOR PACK WITH SMARTPHONE DATA AQUISITION AND TRANSFER

(71) Applicant: Dymedix Corporation, Shoreview, MN (US)

(72) Inventors: James P. Moore, Bloomington, MN (US); Todd M. Eiken, Lindstrom, MN (US)

(73) Assignee: Dymedix Corporation, Shoreview, MN (US)

( * ) Notice: Subject to any disclaimer, the term of this patent is extended or adjusted under 35 U.S.C. 154(b) by 469 days.

(21) Appl. No.: 14/856,637

(22) Filed: Sep. 17, 2015

(65) Prior Publication Data

US 2017/0079580 A1 Mar. 23, 2017

(51) Int. Cl.
| | |
|---|---|
| *G06F 19/00* | (2018.01) |
| *G16H 40/67* | (2018.01) |
| *A61B 5/00* | (2006.01) |
| *A61B 5/024* | (2006.01) |
| *A61B 5/087* | (2006.01) |

(52) U.S. Cl.
CPC .......... *A61B 5/4818* (2013.01); *A61B 5/0022* (2013.01); *A61B 5/024* (2013.01); *A61B 5/0878* (2013.01); *A61B 5/6898* (2013.01); *A61B 5/7225* (2013.01); *G06F 19/00* (2013.01); *G16H 40/67* (2018.01)

(58) Field of Classification Search
CPC ...... G06Q 50/22; G06Q 50/24; A61B 5/4818; A61B 5/0878; A61B 5/024; A61B 5/7225; A61B 5/0022; A61B 5/6898; G06F 19/00; G16H 40/67
See application file for complete search history.

(56) References Cited

U.S. PATENT DOCUMENTS

| 6,845,263 B2 | 1/2005 | Kawaguchi | |
|---|---|---|---|
| 2009/0099471 A1* | 4/2009 | Broadley | G16H 15/00 600/532 |
| 2010/0048985 A1* | 2/2010 | Henke | A61B 5/02055 600/28 |

(Continued)

FOREIGN PATENT DOCUMENTS

| CN | 203749398 | 8/2014 |
|---|---|---|
| CN | 104287700 | 1/2015 |
| WO | WO2014051226 | 4/2014 |

*Primary Examiner* — Joy Chng
(74) *Attorney, Agent, or Firm* — Nikolai & Mersereau, P.A.; Thomas J. Nikolai (57) ABSTRACT

The system of the present invention is intended to provide a simple, out-of-clinic sleep disorders testing tool. It can be used for pretest screening and diagnosis, and post therapy follow-up of patients. The hardware component comprises a disposable sensor pack containing a PVDF airflow sensor and a PVDF pulse wave sensor, each of which is permanently connected to a signal conditioning and communications module configured to communicate with a patient's smartphone via a Bluetooth circuit. An APP stored in the smartphone allows a patient to initiate a diagnostic recording, collect and store digitized data onto the phone and, subsequently, upload data to a secure server for analysis on a host computer following completion of the test.

8 Claims, 5 Drawing Sheets

(56) References Cited

U.S. PATENT DOCUMENTS

| | | |
|---|---|---|
| 2013/0018701 A1* | 1/2013 | Dusig .................... G06Q 30/02 |
| | | 705/7.32 |
| 2013/0030257 A1* | 1/2013 | Nakata ................. A61B 5/0507 |
| | | 600/301 |
| 2013/0046151 A1 | 2/2013 | Bsoul et al. |
| 2013/0144190 A1 | 6/2013 | Bruce et al. |
| 2013/0281883 A1 | 10/2013 | Nishida |
| 2014/0194780 A1* | 7/2014 | Alshaer .................. A61B 7/003 |
| | | 600/586 |
| 2015/0073289 A1 | 3/2015 | Lim |

* cited by examiner

COMBINATION AIRFLOW, SOUND AND PULSE WAVE SENSOR PACK WITH SMARTPHONE DATA AQUISITION AND TRANSFER

CROSS-REFERENCED TO RELATED APPLICATIONS

The present application relates somewhat to application Ser. No. 14/683,509, filed Apr. 10, 2015, and entitled "SCREENING SYSTEM FOR ASSESSING SLEEP ABNORMALITIES".

STATEMENT REGARDING FEDERALLY SPONSORED RESEARCH OR DEVELOPMENT

Not applicable

BACKGROUND OF THE INVENTION

I. Field of the Invention

This invention relates generally to an apparatus and method for conducting a home diagnostic testing and screening for sleep related disturbances and, more particularly, to a system that utilizes a patient's own smartphone as a data acquisition and data transfer device.

II. Discussion of the Prior Art

Obstructive sleep apnea is the most common sleep disorder and is responsible for more mortality and morbidity than any other sleep disorder. Sleep apnea is characterized by recurrent failures to breath adequately during sleep, primarily due to obstructions in the upper airway.

Apnea is defined as a complete cessation of airflow. A related sleep disorder, termed hypopnea, is defined as a reduction in airflow disproportionate to the amount of respiratory effort expended and insufficient to meet the individual's metabolic needs. During episodes of apnea or hypopnea, oxygen levels in the brain decrease while the carbon dioxide level rises. This causes the sleeper to awaken. The brief arousals to breath are followed by a return to sleep.

Obstructive sleep apnea is a serious, yet treatable, health problem worldwide. Published reports indicate that untreated obstructive sleep apnea patients are three to five times more likely to be involved in industrial and motor vehicle accidents and have impaired vigilance and memory. Untreated apnea leads to hypertension, stroke, heart failure, heart attacks and other maladies.

The current standard for the diagnosis of obstructive sleep apnea is a relatively expensive overnight sleep study in a hospital or clinic. Here, a variety of physiologic sensors typically involving electroencephalograms, respiratory airflow, respiratory effort, oxygen saturation, snore sounds and body position are fed into an instrument called a polysomnograph (PSG).

Because of the relative expense involved in having the aforementioned type of sleep study conducted, a need exists for a lower cost way to determine whether a PSG sleep study is needed. As a result, several portable sleep monitors have been developed that can be used in a patient's own home as a screening tool.

While home sleep screening protocols measure significantly fewer physiologic parameters than are typically involved in a PSG-based study, the results of home screening tests that measure respiratory airflow and respiratory effort provide enough information to determine whether a person is a candidate for a comprehensive sleep study or whether there is an immediate need for the patient to acquire and begin use of a CPAP device.

Many industries find it essential that their workers be alert during the execution of their job performance. For example, airline crews, over-the-road truckers and hospital personnel and all those who have the safety of the public as a responsibility should be periodically screened for sleep abnormalities. The expensive testing of thousands of employees in PSG-based sleep labs could prove prohibitively expensive while the cost of running a home sleep screening and diagnostic test can be made sufficiently inexpensive that it can be used to sort out only those employees who test positive for disturbed sleep patterns. Such persons would be encouraged or required to undergo a full sleep study possibly as a condition of continued employment. The present invention provides such a low cost screening and diagnostic testing system for at-home use, one that uses a subject's own smartphone as a data acquisition and data transfer device. Thus, the apparatus of the present invention is intended to test patients for a variety of sleep abnormalities. The outcome of the testing procedure is acceptable as a preliminary risk assessment tool as well as a diagnostic tool for sleep disordered breathing, sleep disruption and in some cases sufficient for prescriptions for therapy.

Users of the present invention may typically be a testing service provider or a business corporation that has a need to make sure that its employees are not compromised due to disturbed sleeping. The patient or employee will apply the sensors and follow the test procedure instructions provided via the subject's own cell phone. Once the digitized sensor data is collected over a predetermined test interval, it will be sent via the cell phone to the host computer where a data analysis program will analyze the data and generate a report.

SUMMARY OF THE INVENTION

In accordance with the present invention, the method for conducting home testing of patients for sleep related disturbances involves first having a testing service firm or an employer business provide the patient or employee with a sensor kit that includes as its components (i) a first polyvinylidene fluoride (PVDF) sensor adapted to be placed on a patient's upper lip for sensing thermal changes due to breathing and episodes of snoring, (ii) and optionally, a second PVDF sensor adapted for placement on a patient's finger for sensing pulse wave amplitude, and (iii) a sensor module to which the first sensor and optionally, the second PVDF sensor is electrically connected. The sensor module includes amplifiers and filters for generating separate wave forms relating to respiration, snoring and possibly pulse wave amplitude variation. The sensor module further includes an analog to digital converter for transforming the analog wave forms into a digital representation thereof for entry into the memory of a microprocessor also forming a part of the sensor module. It, in turn, controls the transmission of data, via a wireless Bluetooth link, to a patient's smartphone.

An application program (APP), which the patient downloads from a host computer of a testing service provider, is stored on the smartphone. It functions to display a sleep test set-up procedure and operating instructions to the patient for display on his or her smartphone screen.

Following set-up in accordance with the displayed set-up instructions, the patient is instructed to activate a "start" button on the smartphone touch screen display and, while subsequently sleeping, the information transmitted to the smartphone from the sensor module is captured and stored in the memory of the smartphone during a test period of a predetermined length. At the conclusion of the test period, the patient is coached to actuate an "upload" icon on the smartphone display screen resulting in the contents of the smartphone memory being sent over the internet to a host computer at the testing service provider's facility where that digitized wave form information is analyzed resulting in the generation of a test report.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which like numerals in the several views referred to corresponding parts.

DESCRIPTION OF THE PREFERRED EMBODIMENT

Figure 1:
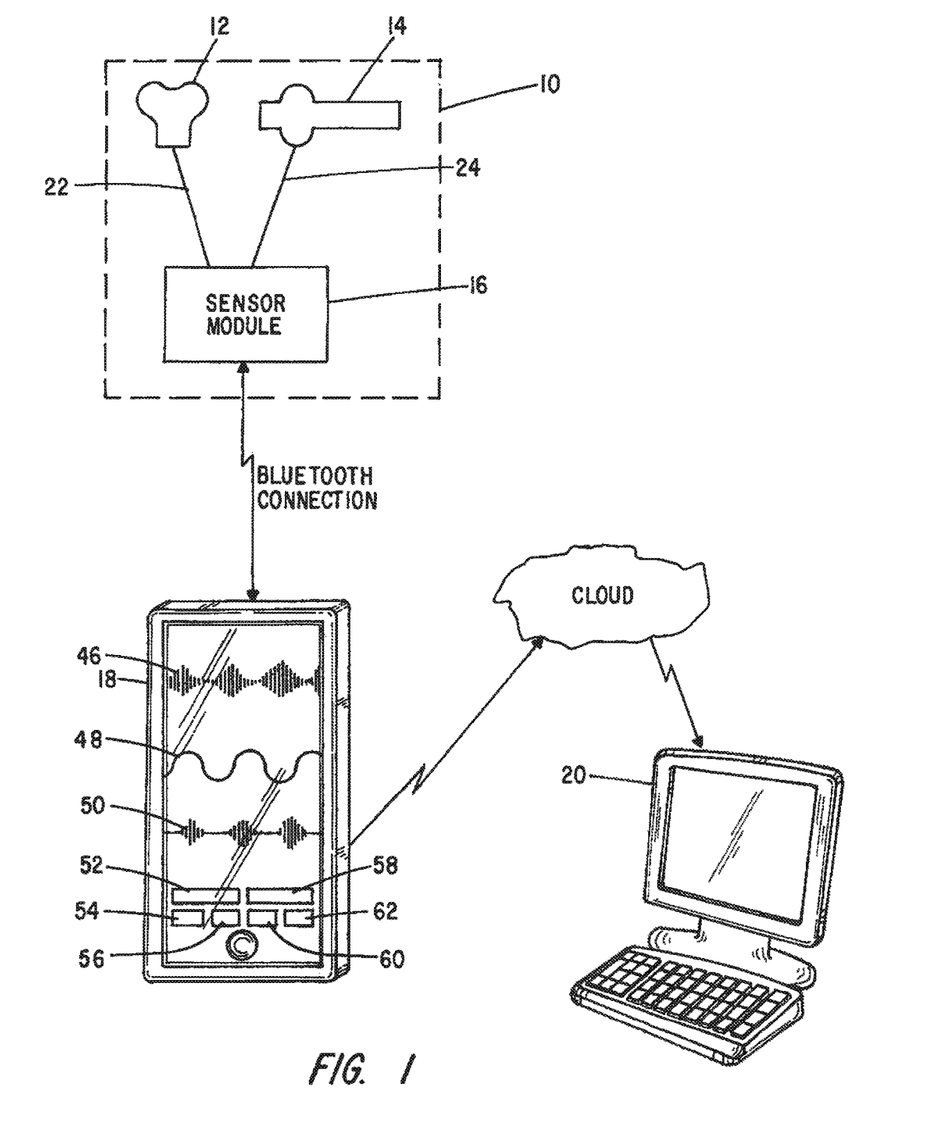
FIG. 1 is a hardware block diagram of a low-cost, disposable sensor kit applied to a patient and capable of transmitting sensor data to the patient's own cell phone.

Referring to FIG. 1, there is illustrated the hardware components comprising the present invention. It comprises a disposable sensor kit shown enclosed by the broken line box 10 and includes an airflow sensor 12, an optional pulse wave amplitude sensor 14 and an electronic sensor module 16. The sensor kits are made available either directly or through an employer by the STSP and are sufficiently inexpensive that they can be disposed of after a single use.

As will be explained in greater detail below, the sensor module 16 is able to communicate over a Bluetooth link to a smartphone 18 which, in turn, is capable of communicating over the internet to a host computer 20, typically located at a sleep testing service provider's location.

The airflow sensor is preferably of a type described in the Stasz U.S. Pat. No. 7,608,047 assigned to the Dymedix Corporation of Shoreview, Minn., and is designed to be worn on a patient's upper lip where it is exposed to respiratory airflow and vibration occasioned by episodes of snoring. The sensor 12 incorporates a polyvinylidene fluoride (PVDF) pyro/piezoelectric transducer and is connected by leads 22 to the sensor module 16.

The pulse wave amplitude sensor 14 also incorporates a PVDF film transducer and is configured to be adhesively affixed to a patient's finger where it responds to the patient's pulse wave resulting from the beating action of his or her heart.

Figure 2:
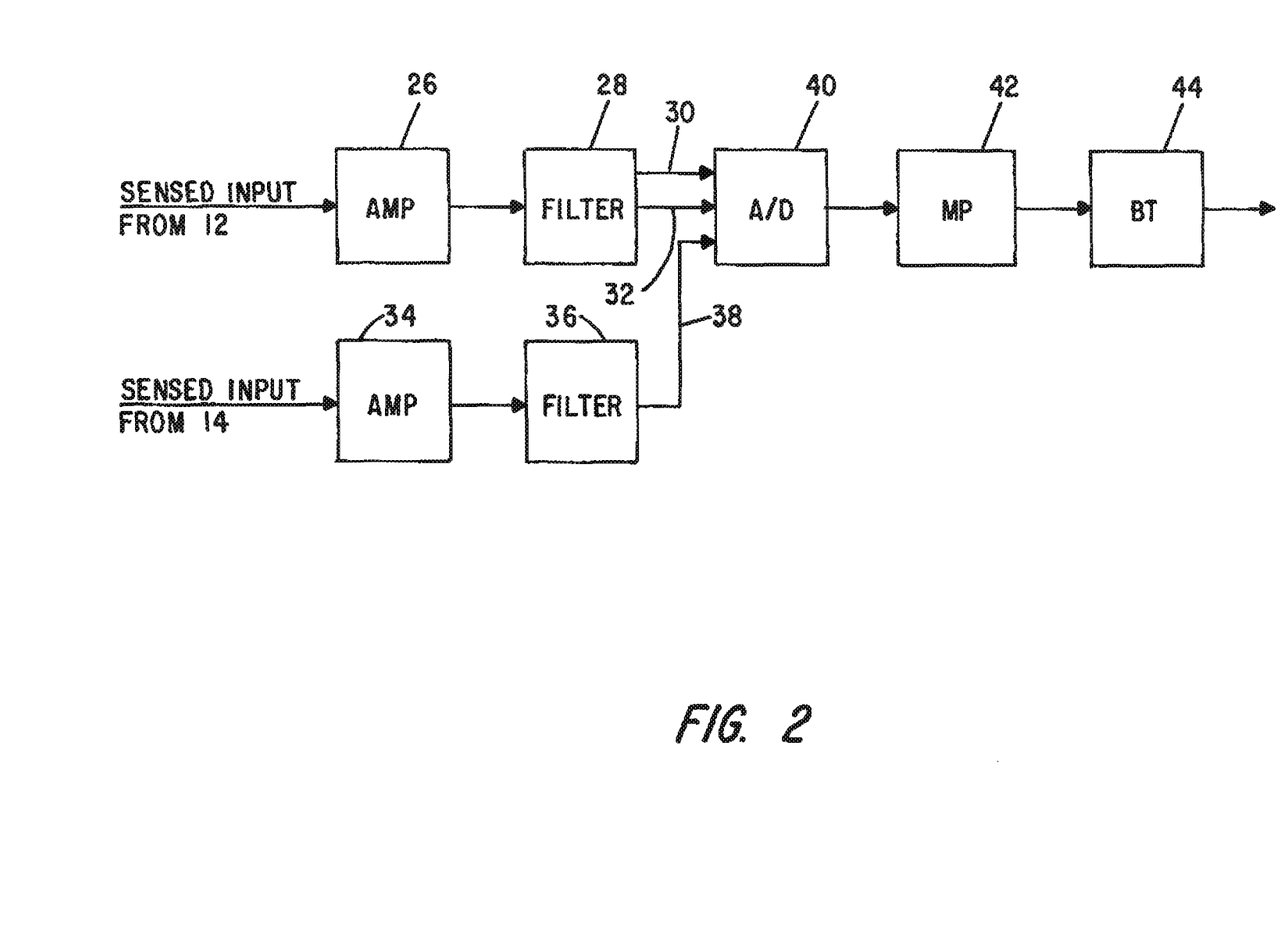
FIG. 2 is a schematic block diagram of the disposable sensor module employed.

FIG. 2 is a block diagram of the circuitry embodied in the sensor module 16. The sensor module is a low power, microprocessor controlled, data acquisition module that filters, preprocesses, and transmits digitized PVDF airflow, snore and pulse wave sensor data to the smartphone. The data is digitally transferred from the sensor module to the receiving smartphone via low power Bluetooth protocol which, in turn, is transmitted by the smartphone 18 via 3g or other communications to a host computer for data analysis and report generation. An input signal from the airflow sensor 12 is first amplified by an amplifier circuit 26 and then applied to a filter network 28 capable of separating the pyro signal of the airflow sensor 12 from the piezo signal from the sensor 12 due to episodes of snoring. It is the temperature variations due to inspiratory and expiratory airflow from the nose and mouth of the patient that produces the pyro signal on output line 30 and the signal due to snoring on the output line 32. Those interested in details of the filter arrangement that can be employed are referred to the Stasz U.S. Pat. No. 6,702,755.

The output from the pulse wave amplitude sensor is applied to an amplifier 34 and a filter network 36 with the resulting output appearing on line 38. The output lines 30, 32 and 38 are applied to an analog-to-digital converter 40, preferably a Texas Instruments TLC2543C integrated circuit. It comprises a 12-bit analog-to-digital converter, a 14-channel multiplexer and microprocessor-compatible control logic. Its 14-channel multiplexer with address logic is capable of directly accessing any of 14 single-ended, analog signals. The A/D converter 40 has a tri-state output latch buffer that provides its output to a microprocessor 42 that has been programmed to store and buffer digital output signals representative of the sensed airflow, the snore and pulse wave amplitude inputs. The microprocessor 42 is preferably equipped with a built-in Bluetooth radio, but in FIG. 2, a Bluetooth adaptor 44 is shown separately.

As those skilled in the art know, Bluetooth is a short-link radio technology device used to create a wireless connection to a smartphone, as indicated in FIG. 1.

With continued reference to FIG. 1, the smartphone 18 may be of a type having the Android operating system or the iPhone operating system commonly referred to as iOS and developed by Apple, Inc. In the case of both the Android operating system and the iOS, the user interface is based on the concept of direct manipulation on a touch screen. Interface control elements consist of sliders, switches and buttons in which gestures such as swipe, tap, pinch and reverse pinch may be used to interact with the device. For purposes of illustration only, in FIG. 1, the smartphone 18 is illustrated as displaying a pulse wave signal 46, an airflow signal 48 and a snore signal 50 on its touch screen. The area on the display labeled 52 may be used to present a signal strength indicator while button areas 54 and 56 may be start and stop switches. The window 58 may be used to present status information while window area 60 may present hours and minutes of a test's duration. Switch 62 may be used to initiate the uploading of data from the smartphone to a remote host computer 20 via the internet.

Available for download from the STSP is an application firmware program commonly referred to as an APP offering the following functionality:

Provide pairing connectivity with the sensor module 16 via the Bluetooth link.

Start/Stop recording via switches 54 and 56.

Record transmitted data from sensor module 16 for a predetermined test time, e.g., 10 hours.

Provide fault instructions to patient and the STSP.

Record non-sensor environmental noise via the microphone of the smartphone and video with audio from the phone camera.

It is further contemplated that software releases will be easily configurable by the STSP to specify varying upload server locations and test sponsoring company names prior to being made available to end user patients.

Figure 3:
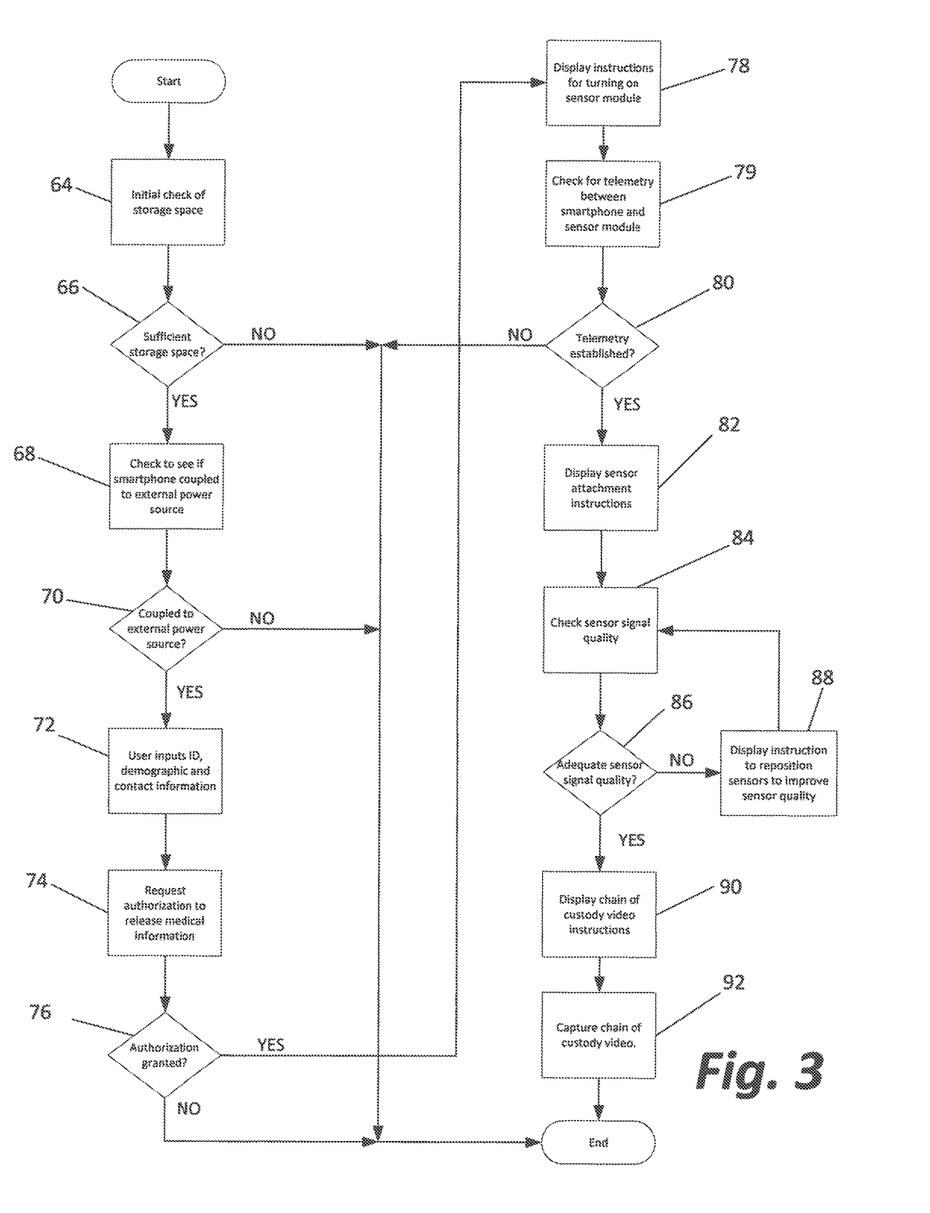
FIG. 3 is a software flow diagram of an application program that may be downloaded from a host computer of a sleep testing service provider (STSP) for installation on a patient's cell phone for setting up the apparatus of FIG. 1 in preparation for an ensuing screening.

The APP also provides easy to understand, step-by-step "Wizard" user interface that walks the patient through each step of the test procedure. FIG. 3 is a software flow diagram of the set-up Wizard forming part of the APP that the patient is instructed to download onto his or her smartphone.

Following a start operation, an initial check of the phone is performed to insure adequate disk space for data storage (Block 64). A test is then made at decision block 66 and, if storage space is insufficient, the setup terminates. If, however, the check determines that the storage space is sufficient, a check is made to see if the smartphone is coupled to an external power source, recognizing that the test may take place over a prolonged period, which would deplete the battery of the smartphone if an external charger was not attached (Block 68 and decision Block 70). At operation block 72, the user is instructed to input an ID, along with demographic and contact information, including email address for return of test results.

Next, at operation block 74 and decision block 76, the patient must provide authorization to release medical information as required by the Federal Health Information Portability and Privacy Act. Provided authorization is granted, and as indicated by block 78 in FIG. 3, the patient is coached by instructions for turning on the sensor module 16 and a check is made of the sensor signal quality to insure correct placement of the sensors 12 and 14 and the continuity of the leads 22 and 24.

The test at decision block 80 indicates that telemetry is established. Next, the patient is provided with text material on the smartphone screen on how to attach the sensors 12 and 14 (Block 82). Once the sensors are attached, the software tests the sensor signal quality at block 84 and, if the signal quality is poor, as determined at decision block 86, the patient is provided with further instructions on how to reposition the sensor to improve sensor quality (Block 88).

Assuming that the sensor signal quality meets predetermined criteria, the patient is instructed to take a video recording of himself or herself, as indicated by operation blocks 90 and 92. This requires the patient to look into the smartphone screen, press the record button and recite a short sentence that is provided to them on the screen, stating their name, current date and time, and stating that they are in fact the person who will be using the device, thus, establishing and documenting a chain of custody.

Figure 4:
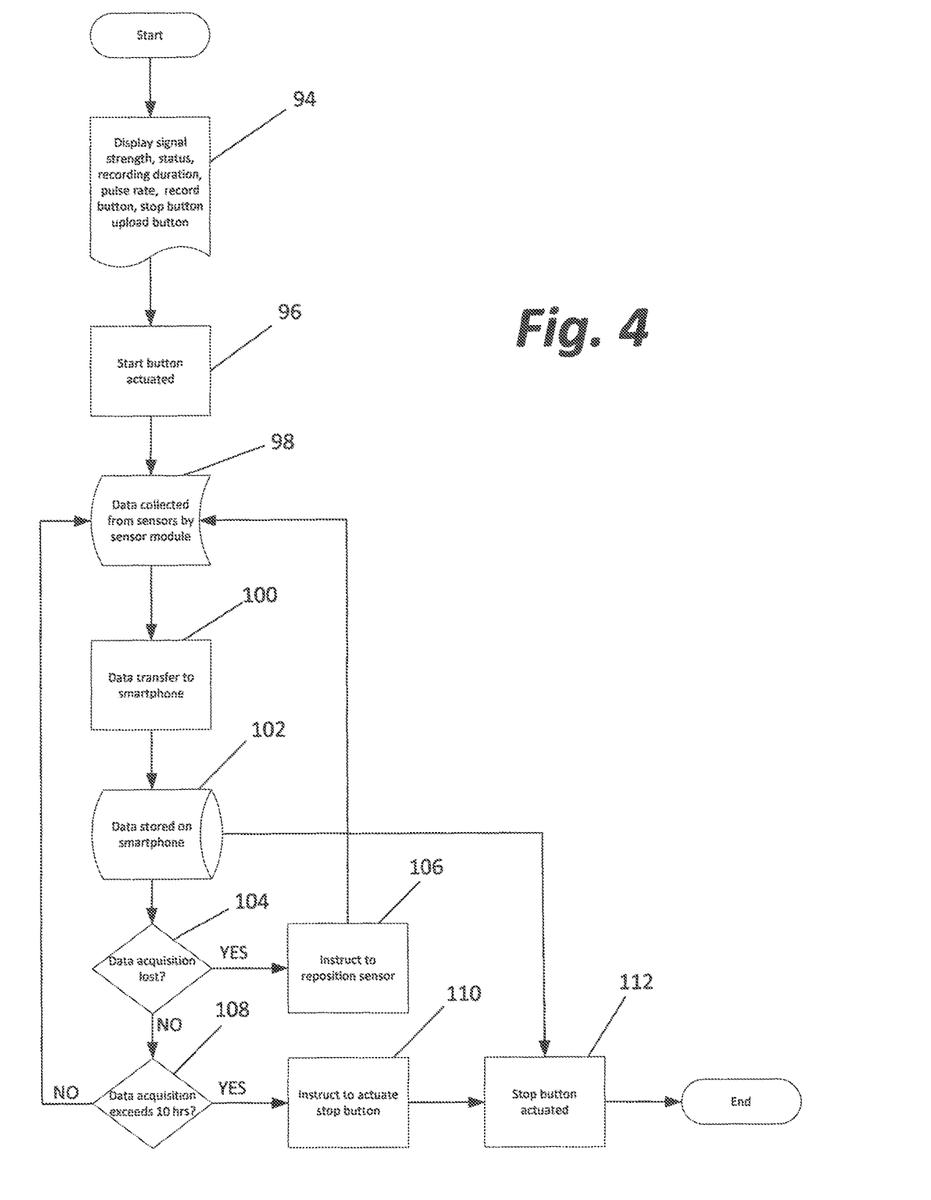
FIG. 4 is a software flow diagram and part of the application (APP) installed on the patient's smartphone for collecting and storing data from the disposable sensor pack of FIG. 1.

Referring next to FIG. 4, it shows the steps involved in the data acquisition stage of the APP. As seen at operation block 94, the signal strength is indicated on the smartphone 18 in the field 52 and the status is displayed in the field 58. For example, the status may be "standby", "recording", "off", or "no Bluetooth". Touching the "start" button 54 initiates recording of the wave form data 46, 48 and 50 in a RAM memory of the microprocessor 42 in the sensor module 16. See Block 98. This digitized wave form data is then transferred over the Bluetooth link to the smartphone (Block 100). It is stored in the memory of the smartphone (Block 102).

During the test interval, a check is periodically made to assure that the data acquisition on the smartphone is not lost. See decision Block 104. If the test at block 104 indicates that data acquisition is lost, the cell phone is made to beep to awake the patient and instructions are provided on how to reposition the sensor to restore data acquisition (Block 106). If data acquisition is not lost, a test is made at decision block 108 on whether 10 hours of sleep data has been acquired. If not, the operation loops back to block 98 where further data is collected. However, if there has been 10 hours of data acquisition, an audible signal is again issued by smartphone and instructions are provided to the patient to press the "stop" button. See Blocks 110 and 112.

Figure 5:
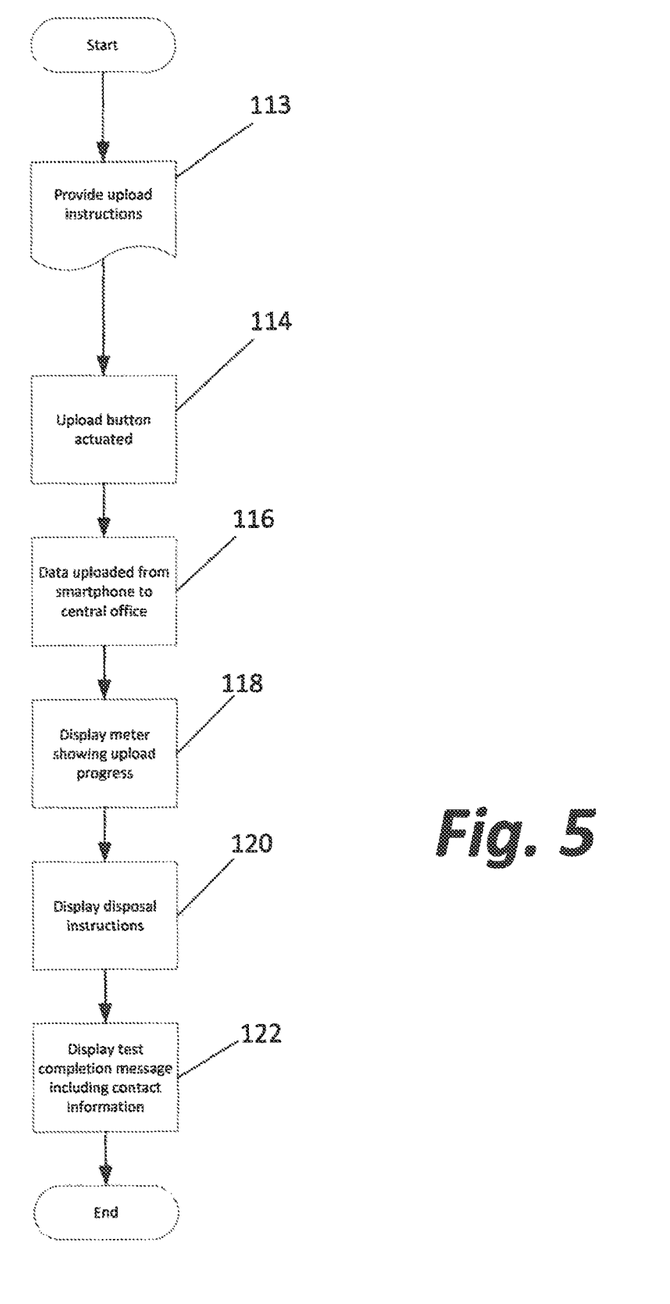
FIG. 5 illustrates the steps of the APP for uploading data from the patient's cell phone to a host computer at the STSP.

The flowchart of FIG. 5 illustrates the operations embodied in the APP downloaded by the smartphone for transferring the collected test data to the remote host computer 20 at the sleep test service provider's facility. At the conclusion of the collection of, for example, 10 hours of sleep test data, a message is provided on the screen of the smartphone for initiating the upload of the data from the smartphone to the remote host computer. Actuation of the upload button (Block 114) establishes a communication protocol between the smartphone and the host computer via the internet. Data, including the recorded wave forms, the demographic information provided by the subject and the audio and video subject identification and verification information is thus uploaded from the smartphone to the host computer (Block 116) while a display meter on the smartphone shows the upload progress (Block 118). Once the data transfer from the smartphone to the host computer is completed, a further message is provided on the smartphone screen providing the patient with instructions on how the data acquisition module 10 is to be disposed of (Block 120). Lastly, a "test completion" message is provided to the patient via the smartphone and contact information of the test provider is presented (Block 122).

The software program executed by the host computer 20 at the testing service provider's facility for analyzing the received wave forms and producing a study report is more particularly described in co-pending application Ser. No. 14/683,509, filed Apr. 10, 2015, the contents of which are hereby incorporated by reference.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices. Also, various modifications, both as to the equipment and operating procedures, can be accomplished without departing from the scope of the invention itself.

What is claimed is:

1. A method for conducting home testing and screening of patients for sleep related disturbances comprising the steps of:
   a. providing the patients with a sensor kit including at least one polyvinylidene fluoride (PVDF) sensors and a sensor module, the at least one PVDF sensor adapted to be appended to an upper lip area of a patient and exposed to thermal changes due to respiratory air flow and to vibration due to episodes of snoring, the sensor module being electrically connected to the at least one PVDF sensor and including (i) an amplifier and a filter for producing analog signal waveforms corresponding to respiratory air flow and snoring episodes, (ii) an analog-to-digital converter coupled to receive said analog signal waveforms for converting same to a digital format, (iii) a microprocessor with inputs connected to receive digitized waveforms from the analog to digital converter and temporarily storing same, and (iv) a Bluetooth radio transmitter coupled to and controlled by the microprocessor for communicating wirelessly to a patient supplied smartphone;

b. downloading an application program from a host computer at a testing service provider facility to the patient supplied smartphone, the application program operative to effect a display of sleep test set-up procedures and operating instructions to the patient on a display of the smartphone;

c. initiating a test by the patient activating a start button on the smartphone following set-up in accordance with the displayed set-up procedures and operating instructions;

d. capturing and storing in a memory of the smartphone digitized waveforms sent from the sensor module over a predetermined test period; and e. at a conclusion of the test period, transmitting contents of the smartphone memory to the host computer at the testing service provider facility for analysis and generation of a test report.

2. The method of claim 1 wherein said sleep test set-up procedures comprise the steps of:

a. determining storage space availability on the smartphone;

b. assessing power availability for the smartphone;

c. requesting entry of patient demographic information by the patient into the smartphone;

d. obtaining authorization from the patient for compliance with laws relating to release of medical information; and e. checking the signal quality of the sensor module output.

3. The method of claim 1 wherein the step of capturing and storing digitized waveforms comprises:

a. collecting data from the at least one sensor in the microprocessor memory in the sensor module;

b. transferring the collected data to a memory in the smartphone;

c. continuously testing the collected data transfer for break in communication and providing instructions to patient to reposition the at least one PVDF sensor upon detection of break; and d. instructing the patient to depress a "stop" icon on his smartphone upon completion of a predetermined recording period.

4. The method of claim 1 wherein the step of transmitting contents of smartphone memory to the host computer comprises:

a. presenting upload instructions to the patient on the smartphone display screen;

b. actuating an "upload" icon on the smartphone display screen;

c. displaying on the smartphone an indicator reflecting progress of the upload; and d. providing a test completion message and test service provider contact information to the patient by way of his or her smartphone.

5. The method of claim 2 wherein the demographic information is uploaded to the host computer with the digitized waveforms sent from the sensor module.

6. The method of claim 1 wherein the application program effects collection and storage in the smartphone of a video selfie and audio information from a smartphone's camera to establish a patient's chain of custody.

7. The method of claim 1 wherein the application program effects presentation on the smartphone display screen of Bluetooth signal strength, recording status, current recording duration and upload progress.

8. The method of claim 1 and further including a further PVDF sensor adapted to be affixed to the patient's phalanges and exposed to the patient's pulse wave, said further sensor being connected to the sensor module.

* * * * *